US009733163B2

(12) United States Patent
Berberich et al.

(10) Patent No.: US 9,733,163 B2
(45) Date of Patent: *Aug. 15, 2017

(54) HOLDING APPARATUS FOR RECEIVING SPECIMEN SLIDES

(71) Applicant: Leica Biosystems Nussloch GmbH, Nussloch (DE)

(72) Inventors: Markus Berberich, Heidelberg (DE); Christian Wilke, Rimbach (DE); Jurgen Tenhaef, Brombachtal (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,364

(22) Filed: Mar. 10, 2016

(65) Prior Publication Data

US 2016/0187236 A1 Jun. 30, 2016

Related U.S. Application Data

(63) Continuation of application No. 13/313,054, filed on Dec. 7, 2011, now Pat. No. 9,322,754.

(30) Foreign Application Priority Data

Dec. 7, 2010 (DE) .......................... 10 2010 062 543

(51) Int. Cl.
| | | |
|---|---|---|
| *B65D 73/00* | (2006.01) | |
| *G01N 1/31* | (2006.01) | |
| *G01N 35/00* | (2006.01) | |
| *B65D 85/48* | (2006.01) | |

(52) U.S. Cl.
CPC ............... *G01N 1/31* (2013.01); *B65D 85/48* (2013.01); *G01N 35/00732* (2013.01)

(58) Field of Classification Search
CPC ..... G01N 1/31; G01N 35/00732; B65D 85/48
USPC ........................................................ 206/464
See application file for complete search history.

(56) References Cited

U.S. PATENT DOCUMENTS

| | | | |
|---|---|---|---|
| 1,381,476 A | 6/1921 | Lane | |
| 3,099,980 A | 8/1963 | Merkle | |
| 3,685,647 A | 8/1972 | Erickson | |
| 3,701,558 A | 10/1972 | Baker | |
| 3,861,733 A | 1/1975 | Vander | |
| 4,643,879 A | 2/1987 | Hanaway | |

(Continued)

FOREIGN PATENT DOCUMENTS

| | | |
|---|---|---|
| DE | 4117831 | 12/1992 |
| EP | 0884577 | 12/1998 |

(Continued)

OTHER PUBLICATIONS

United Kingdom Intellectual Property Office, Combined Search and Examination Report mailed Feb. 20, 2012 in corresponding British Patent Application No. GB1120441.9 Feb. 20, 2012.

(Continued)

*Primary Examiner* — Anthony Stashick
*Assistant Examiner* — James M Van Buskirk
(74) *Attorney, Agent, or Firm* — Hodgson Russ LLP

(57) ABSTRACT

The present invention relates to a holding apparatus (10) for receiving specimen slides (1), having a holder (3, 4, 5) for handling the holding apparatus (10) and having at least two identification units (2a, 2b) that make available different information items to enable characterization of the orientation of the holding apparatus (10) in a stainer or coverslipper.

19 Claims, 1 Drawing Sheet

(56) References Cited

U.S. PATENT DOCUMENTS

| | | |
|---|---|---|
| 4,719,087 A | 1/1988 | Hanaway |
| 4,975,250 A | 12/1990 | Mordecki |
| 5,270,012 A | 12/1993 | Kanamori et al. |
| 5,573,727 A | 11/1996 | Keefe |
| 5,663,545 A | 9/1997 | Marquiss |
| 6,094,301 A | 7/2000 | Dreyer et al. |
| 6,156,575 A | 12/2000 | Fassbind et al. |
| 6,486,780 B1 | 11/2002 | Garber et al. |
| 6,635,225 B1 | 10/2003 | Thiem et al. |
| 7,070,053 B1 | 7/2006 | Abrams et al. |
| 7,160,514 B2 | 1/2007 | Chouinard et al. |
| 7,706,061 B2 | 4/2010 | Tafas |
| 7,829,028 B2 | 11/2010 | Elsener et al. |
| 3,182,763 A1 | 5/2012 | Duffy et al. |
| 2002/0018733 A1 | 2/2002 | Kapplein et al. |
| 2005/0107934 A1 | 5/2005 | Gudat et al. |
| 2005/0179999 A1 | 8/2005 | Dooling |
| 2005/0246094 A1 | 11/2005 | Moscatiello |
| 2007/0042340 A1 | 2/2007 | Konomen et al. |
| 2007/0205126 A1 | 9/2007 | Elsener et al. |
| 2007/0242349 A1 | 10/2007 | Tafas |
| 2007/0269347 A1 | 11/2007 | Stanchfield et al. |
| 2009/0136386 A1 | 5/2009 | Duffy et al. |
| 2009/0281419 A1 | 11/2009 | Troesken et al. |
| 2010/0083777 A1 | 4/2010 | Walter et al. |
| 2010/0086964 A1 | 4/2010 | Walter et al. |
| 2011/0095864 A1 | 4/2011 | Trueeb et al. |
| 2013/0065315 A1 | 3/2013 | Safar et al. |

FOREIGN PATENT DOCUMENTS

| | | |
|---|---|---|
| EP | 1659388 | 5/2006 |
| JP | 2167473 | 6/1990 |
| JP | H07-260649 | 10/1995 |
| JP | 2002-323505 | 11/2002 |
| WO | 0196193 | 12/2001 |

OTHER PUBLICATIONS

Leica Microsystems: Leica CV5030 Robotic Coverslipper Operating Manual; Germany; Aug. 2008. Aug. 1, 2008.

Leica Microsystems: Leica CV5030 Glass Coverslipper for Histology and Cytology; Germany; Jun. 2009. Jun. 1, 2009.

HOLDING APPARATUS FOR RECEIVING SPECIMEN SLIDES

CROSS REFERENCE TO RELATED APPLICATIONS

This application is a continuation of U.S. application Ser. No. 13/313,054 filed Dec. 7, 2011, which claims priority of German patent application number 10 2010 062 543.4-52 filed Dec. 7, 2010, the entire disclosures of which are incorporated by reference herein.

FIELD OF THE INVENTION

The present invention relates to a holding apparatus for receiving specimen slides.

BACKGROUND OF THE INVENTION

Holding apparatuses (called "racks") are used in the medical field to receive a plurality of specimen slides having samples or smears located on them. Holding apparatuses having two holders are known in the existing art, as shown in the brochure entitled "Leica ST5020 Multistainer and Leica CV5030 Glaseindeckautomaten [glass coverslippers]", February 2003, order no. 0705-2-1-104, or in DE 100 10 140 A1. The holders are embodied as hooks so that the holding apparatus can be hooked into a corresponding receptacle inside a stainer or coverslipper. An identification unit is integrated into the holding apparatus for identification of the holding apparatus. This allows the processing machine, for example, to read out information regarding the nature of the coverslipping or staining operation to be carried out.

The known holding apparatuses have disadvantages as a result of their configuration. For example, the specimen slides sorted into the holder are concealed in part by the holders, thus complicating (in particular, automatic) inspection and monitoring of the specimen slides.

In addition, the two holders are relatively unstable and offer only a limited handling capability for the holding apparatus. Furthermore, while the specimen slides are readily accessible from above for introduction and removal, they are also not protected from falling out.

Incorrect orientation of the holding apparatus can moreover occur when the holding apparatus is hooked into a corresponding receptacle of a processing machine. This is understood to mean that the holding apparatus is inserted into the machine 180 degrees askew. If the holding apparatus is hooked in the wrong way around, the specimen slides are, for example, in particular coverslipped on the wrong side in the coverslipping process and thus become substantially unusable. Other functionalities that rely on correct orientation of the specimen slides, for example checking of the specimen slides, are also disabled in such a case.

It is therefore desirable to have the capability to eliminate the aforementioned disadvantages, in particular, the capability to detect an incorrect orientation and to increase ease of handling.

SUMMARY OF THE INVENTION

According to the present invention, a holding apparatus having a holder for handling the holding apparatus, and having at least two identification units, is used to receive specimen slides. The at least two identification units contain different information items that can be read out, with the result that, in particular, different points (e.g. "front" or "back") on the holding apparatus can be characterized, enabling detection of the orientation of the holding apparatus in, for example, a receptacle. The different information items can be used only to characterize the orientation, but preferably are used also for further purposes, as described e.g. in DE 100 10 140 A1 recited above.

By preference, at least one of the at least two identification units furnishes information items relating to the specimen slides contained in the holding apparatus and/or relating to a treatment in a stainer or coverslipper. According to the present invention, another one of the at least two identification units furnishes other information items that, however, can in principle also relate to the specimen slides contained in the holding apparatus and/or to a treatment in a stainer or coverslipper. The other information items can, however, also serve merely to characterize a specific point on the holding apparatus (e.g. "front" or "back"). If only one readout device is provided in a processing machine for treating the specimen slides held in the holding apparatus, the correct orientation can be detected on the basis of the information that is read out. If the device reads out "correct" information (e.g. the above-described information items relating to the specimen slides contained in the holding apparatus and/or relating to a treatment in a stainer or coverslipper), proper orientation is simultaneously recognized. If the device reads out "wrong" information (e.g. "back"), improper orientation is recognized. It is thus possible, on the basis of a first identification unit, to detect the orientation of the holding apparatus while additional information items regarding coverslipping and staining, and/or further data regarding the holding apparatus, can be stored on the basis of a second identification unit.

One of the different information items can also be used, particularly advantageously, to unequivocally characterize the holding apparatus. The holding apparatus can thereby be allocated to a specific treatment in a processing machine. On the other hand, it is also possible to keep a kind of logbook about the holding apparatus and the specimen slides held therein. This is very advantageous in particular for the medical field, since it is thereby possible to understand what has happened with the holding apparatus and specimen slides, and where.

According to a preferred embodiment, the identification units are RFID transponders. RFID transponders are available as very small units, so they can be incorporated into the holding apparatus without making it heavier or modifying its shape. A further reason for using RFID transponders may be seen in their low manufacturing and acquisition costs, and their robustness and reliability, thus improving capabilities especially in the medical field, where many chemicals etc. are worked with.

In a preferred embodiment, a first identification unit is attached at a first point, and a second identification unit at a second point that is symmetrical with respect to the first point in terms of a 180-degree rotation around a vertical axis of the holding apparatus. This on the one hand facilitates characterization of the orientation, and on the other avoids the possibility of mutual interference between the two identification units.

If the holder is embodied asymmetrically, this offers a further simple capability for detecting the orientation of the holding apparatus. The asymmetry is advantageously also designed so that the holder at least does not impede or complicate visual monitoring of the specimen slides held in the holding apparatus.

If the holder is embodied as a structural unit in the form of a bracket, this on the one hand increases the stability of the holder and thus the ease of handling of the holding apparatus, and on the other hand offers protection for the specimen slides (for example, to prevent falling out) if the bracket extends so that it impedes or prevents removal. To allow the specimen slides nevertheless to be inserted and removed, the holder is advantageously embodied in foldable fashion, so that it can be positioned so as not to impede or prevent removal.

A particularly preferred foldable holder, which at the same time is embodied asymmetrically, can preferably be folded over in only one direction. If the holding apparatus is inserted in skewed fashion into a machine, the machine is then not capable of folding the holder over to the desired side. The holder would be blocked, and the incorrect orientation would likewise be detected.

The holder can furthermore be embodied so that it forms a structural unit made up of multiple elements. The holder preferably encompasses a bottom, a top, and a frame. A continuous frame results in a high level of stability for the entire holding apparatus, with the top and bottom simultaneously forming one handling unit. At least two identification units can be arranged on the bottom of the holder or can be arranged on the top.

Further advantages and embodiments of the invention are evident from the description and the accompanying drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

The invention is schematically depicted in the drawings on the basis of an exemplifying embodiment, and will be described in detail below with reference to the drawings.

DETAILED DESCRIPTION OF THE INVENTION

Figure 1:
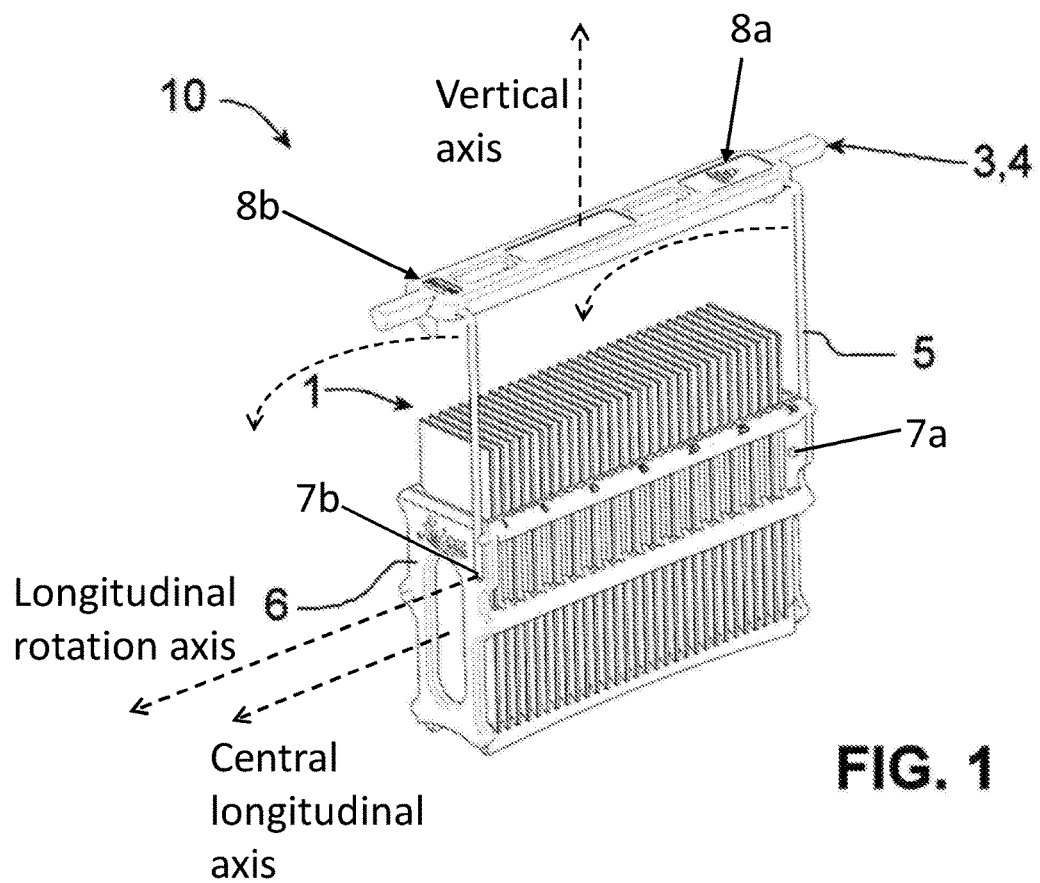
FIG. 1 shows a preferred holding apparatus according to the invention, having a plurality of specimen slides.
Figure 2:
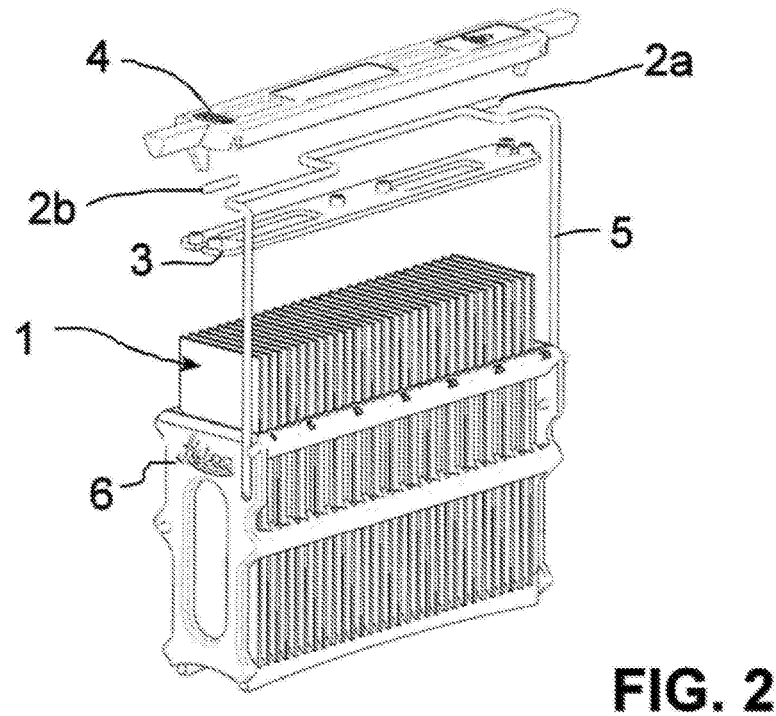
FIG. 2 is an exploded drawing of the preferred holding apparatus according to FIG. 1.

FIGS. 1 and 2 are described together, identical elements being labeled with identical reference characters.

FIG. 1 shows a holding apparatus 10 (a so-called "rack") having a receiving element 6 in which specimen slides 1 can be sorted into compartments. Receiving element 6 can have a numbering system so that the number of specimen slides 1 introduced can easily be read off on the basis of said numbering. Receiving element 6 that is shown can store, for example, up to thirty specimen slides. A holder 3, 4, 5 is mounted on receiving element 6. The holder encompasses a bottom 3, a top 4, and a frame 5, the top-bottom system forming a handling unit and being arranged above specimen slides 1 on frame 5.

Holder 10 further comprises two identification units, embodied here as RFID transponders 2a and 2b, that are provided in order to characterize the orientation of holding apparatus 10 and provide different information items therefor. In the embodiment shown, a first RFID transponder 2a comprises information for characterizing the orientation of the holding apparatus in processing machines. A second RFID transponder 2b comprises information for unequivocal identification of the holding apparatus. Holding apparatus 10 can thus, for example, be allocated to a treatment in a processing machine. A logbook can also be created. The RFID transponders can be read out by a corresponding reading device in the processing machine.

FIG. 2 shows, by way of an exploded view, the individual parts of holder 3, 4, 5 of holding apparatus 10. Top 4 of the holder comprises two cutouts by means of which holding apparatus 10 can be picked up by a gripper of a processing machine and, for example, transported to the next station within the machine.

First RFID transponder 2a is mounted or arranged at a first point 8a, and second RFID transponder 2b at a second point 8b, on or in holder 3, 4, 5, in particular between bottom 3 and top 4.

Frame 5 firstly runs perpendicularly upward from its mounting points 7a, 7b on receiving element 6 and then extends horizontally. It can be manufactured from metal or plastic. Frame 5 is formed asymmetrically and attached to receiving element 6 of holding apparatus 10 eccentrically, in such a way that it can be folded over only to one side (in the Figure, to the left). When frame 5 or holder 3, 4, 5 is folded over to the desired side, specimen slides 1 are readily accessible and can conveniently be sorted into holding apparatus 10 or removed therefrom.

In order to enhance the stability of the holder, bottom 3, top 4, and frame 5 are assembled so as to form one structural unit. Bottom 3 and top 4 have clamping means or snap-in means for this purpose, such that when bottom 3 is joined to top 4, the two RFID transponders 2a and 2b, as well as frame 5, are clamped in between bottom 3 and top 4.

What is made available in the context of the invention is a holding apparatus that on the one hand offers protection and stability, and on the other hand allows prompt detection of skewed insertion of the holding apparatus.

The invention is not to be limited to the specific embodiments disclosed, and modifications and other embodiments are intended to be included within the scope of the invention.

What is claimed is:

1. A holding apparatus (10) comprising:
    a receiving element configured to receive specimen slides (1);
    a holder (3, 4, 5) for handling of the holding apparatus (10), the holder (3, 4, 5) being pivotally connected to the receiving element via two mounting points, the two mounting points defining an axis which the holder is rotatable about, wherein the holder is rotatable between a first position and a second position; and
    at least two identification units (2a, 2b) located on the holder, each identification unit having unique information items for characterizing an orientation of the holding apparatus (10) in a stainer or coverslipper, wherein the identification units include RFID transponders (2a, 2b), and wherein the unique information items in one of the at least two identification units (2a, 2b) characterizes a front of the holding apparatus (10) or a back of the holding apparatus (10);
    wherein in the first position, the holder prevents removal of the specimen slides from the receiving element, and in the second position, the holder allows the specimen slides to be removed from the receiving element.

2. The holding apparatus (10) according to claim 1, wherein a first identification unit (2a) of the at least two identification units (2a, 2b) is attached at a first point and a second identification unit (2b) of the at least two identification units (2a, 2b) is attached at a second point.

3. The holding apparatus (10) according to claim 2, wherein the holding apparatus (10) has a vertical axis, the second point being located 180-degrees about the vertical axis from the first point so that the first point is symmetric with the second point with respect to the vertical axis.

4. The holding apparatus (10) according to claim 1, wherein the holder (3, 4, 5) has an asymmetrical shape.

5. The holding apparatus (10) according to claim 1, wherein the holder (3, 4, 5) is a bracket.

6. The holding apparatus (10) according to claim 1, wherein the holder (3, 4, 5) of the holding apparatus (10) is foldable.

7. The holding apparatus (10) according to claim 1, wherein the holder (3, 4, 5) comprises a bottom (3), a top (4), and a frame (5).

8. The holding apparatus (10) according to claim 7, wherein the at least two identification units (2a, 2b) are arranged on the bottom (3) of the holder (3, 4, 5).

9. The holding apparatus (10) according to claim 7, wherein the at least two identification units (2a, 2b) are arranged on the top (4).

10. The holding apparatus (10) according to claim 7, wherein the at least two identification units (2a, 2b) are arranged between the bottom (3) and the top (4).

11. The holding apparatus (10) according to claim 1, wherein the holder (3, 4, 5) is mounted eccentrically on two oppositely located sides of the holding apparatus (10), wherein a first portion of the holder (3, 4, 5) extends upwardly, away from the two oppositely located sides, and a second portion of the holder (3, 4, 5) extends perpendicularly away from the first portion of the holder (3, 4, 5).

12. The holding apparatus (10) according to claim 1, wherein at least one of the at least two identification units (2a, 2b) has information items relating to the holding apparatus.

13. The holding apparatus (10) according to claim 1, wherein at least one of the at least two identification units (2a, 2b) has information items relating to specimen slides (1) received by the holding apparatus (10).

14. The holding apparatus (10) according to claim 1, wherein at least one of the at least two identification units (2a, 2b) has information items relating to a treatment in a stainer or coverslipper.

15. The holding apparatus (10) according to claim 1, wherein at least one of the at least two identification units (2a, 2b) makes available information items relating to the holding apparatus (10), relating to specimen slides (1) received by the holding apparatus (10), and relating to a treatment in a stainer or coverslipper.

16. A holding apparatus (10) comprising:
a receiving element configured to receive specimen slides (1);
a holder (3, 4, 5) for handling of the holding apparatus (10), the holder (3, 4, 5) being pivotally connected to the receiving element via two mounting points, the two mounting points defining an axis which the holder is rotatable about, wherein the holder is rotatable between a first position and a second position; and
at least two identification units (2a, 2b) located on the holder, each identification unit having unique information items for characterizing an orientation of the holding apparatus (10) in a stainer or coverslipper, wherein the identification units include RFID transponders (2a, 2b), and wherein the unique information items in one of the at least two identification units (2a, 2b) characterizes a front of the holding apparatus (10) or a back of the holding apparatus (10);
wherein in the first position, the holder prevents removal of the specimen slides from the receiving element, and in the second position, the holder allows the specimen slides to be removed from the receiving element, wherein a first identification unit (2a) of the at least two identification units (2a, 2b) is attached at a first point and a second identification unit (2b) of the at least two identification units (2a, 2b) is attached at a second point, and wherein the holding apparatus (10) has a vertical axis, the second point being located 180-degrees about the vertical axis from the first point so that the first point is symmetric with the second point with respect to the vertical axis.

17. The holding apparatus (10) according to claim 16, wherein at least one of the at least two identification units (2a, 2b) makes available information items relating to one or more of the holding apparatus (10), specimen slides (1) received by the holding apparatus (10), or a treatment in a stainer or coverslipper.

18. A holding apparatus (10) comprising:
a receiving element configured to receive specimen slides (1);
a holder (3, 4, 5) for handling of the holding apparatus (10), the holder (3, 4, 5) being pivotally connected to the receiving element via two mounting points, the two mounting points defining a longitudinal rotation axis which the holder is rotatable about, wherein the longitudinal rotation axis is offset from a central longitudinal axis of the receiving element, wherein the holder is rotatable between a first position and a second position; and
at least two identification units (2a, 2b) located on the holder, each identification unit having unique information items for characterizing an orientation of the holding apparatus (10) in a stainer or coverslipper, wherein the identification units include RFID transponders (2a, 2b), and wherein the unique information items in one of the at least two identification units (2a, 2b) characterizes a front of the holding apparatus (10) or a back of the holding apparatus (10);
wherein in the first position, the holder prevents removal of the specimen slides from the receiving element, and in the second position, the holder allows the specimen slides to be removed from the receiving element.

19. The holding apparatus (10) according to claim 18, wherein at least one of the at least two identification units (2a, 2b) makes available information items relating to one or more of the holding apparatus (10), specimen slides (1) received by the holding apparatus (10), or a treatment in a stainer or coverslipper.

* * * * *